(12) United States Patent
Hancu et al.

(10) Patent No.: US 7,282,615 B2
(45) Date of Patent: Oct. 16, 2007

(54) CATALYST COMPOSITIONS AND THEIR USE FOR CHLORINATING AROMATIC COMPOUNDS

(75) Inventors: Dan Hancu, Clifton Park, NY (US); Robert Edgar Colborn, Niskayuna, NY (US); Richard Joseph Kilmer, Charlton, NY (US); John Patrick Lemmon, Schoharie, NY (US)

(73) Assignee: SABIC Innovative Plastics, IP BV

( * ) Notice: Subject to any disclaimer, the term of this patent is extended or adjusted under 35 U.S.C. 154(b) by 653 days.

(21) Appl. No.: 10/870,351

(22) Filed: Jun. 16, 2004

(65) Prior Publication Data

US 2005/0283033 A1  Dec. 22, 2005

(51) Int. Cl.
*C07C 17/00* (2006.01)
*C07C 22/00* (2006.01)
(52) U.S. Cl. ........................ 570/207; 570/182
(58) Field of Classification Search ................ 570/182, 570/207
See application file for complete search history.

(56) References Cited

U.S. PATENT DOCUMENTS

| | | | |
|---|---|---|---|
| 3,226,447 A | 12/1965 | Bing et al. | |
| 3,622,640 A | 11/1971 | Taylor et al. | |
| 4,031,142 A | 6/1977 | Graham | |
| 4,031,145 A | 6/1977 | Di Bella | |
| 4,031,146 A | 6/1977 | DiBella | |
| 4,031,147 A | 6/1977 | Graham | |
| 4,190,609 A | 2/1980 | Lin | |
| 4,250,122 A | 2/1981 | Lin et al. | |
| 4,289,916 A | 9/1981 | Nakayama et al. | |
| 4,647,709 A | 3/1987 | Wolfram | |
| 4,925,994 A | 5/1990 | Mais et al. | |
| 5,210,343 A | 5/1993 | Mais et al. | |

FOREIGN PATENT DOCUMENTS

EP  0 126 669  11/1984

OTHER PUBLICATIONS

International Search Report dated Nov. 18, 2005.

*Primary Examiner*—J. Parsa

(57) ABSTRACT

A method for ring-halogenating an aromatic compound comprises contacting the aromatic compound with chlorine or bromine in the presence of a catalyst composition, where the catalyst composition comprises at least one salt comprising a metal selected from the group consisting of Group 13 metal; and a counterion derived from an acid having a pKa relative to water of 0 or greater; and at least one organic sulfur compound.

9 Claims, No Drawings

CATALYST COMPOSITIONS AND THEIR USE FOR CHLORINATING AROMATIC COMPOUNDS

BACKGROUND

This invention relates to the chlorination of aromatic compounds. More particularly, it relates to chlorination methods and catalyst compositions capable of producing predominantly para-chloro aromatic compounds.

Chlorination of aromatic compounds such as toluene and xylenes is a known reaction affording useful compounds. The most useful of these compounds for many purposes are the para-chloro aromatic compounds. para-Chlorotoluene, for example, is an intermediate capable of conversion into many useful chemicals. para-Chloro-ortho-xylene (also sometimes referred to as 4-chloro-1,2-dimethylbenzene or 4-chloro-o-xylene) is another useful compound, which can be oxidized to 4-chlorophthalic acid, which is in turn an important intermediate in the production of polyetherimides. However, the production of these useful para-chloroaromatic compounds is complicated by the simultaneous production of numerous undesirable by-products. Thus, chlorination of toluene and xylenes (ortho-xylene and ortho-xylene) produces the para-monochloro isomer in admixture with other isomers, such as ortho-chlorotoluene and 3-chloro-1,2-dimethylbenzene, respectively. In addition, numerous polychlorinated products are also generally produced.

Many of the known methods for chlorination of aromatic compounds involve reaction with elemental chlorine in the presence of Lewis acids, such as for example, ferric chloride, antimony trichloride, antimony pentachloride, zinc chloride and aluminum chloride, which are also generally used as catalysts in Friedel-Crafts reactions, such as alkylation and acylation.

However, the use of such catalysts generally does not lead to excellent selectivity for the desired para-chloroaromatic isomer and minimized formation of polychlorinated products. Various publications, including many U.S. patents, go further in describing mixed catalyst systems in which another catalyst component is an organosulfur compound. The organosulfur compounds disclosed in these publications are of very diverse structures. Some examples of organosulfur compounds that have been used include phenoxathiins, thianthrenes, and phenothiazines. Illustrative patents are U.S. Pat. Nos. 3,226,447, 4,031,142, 4,031,145, 4,031,147, 4,190,609, 4,250,122, 4,289,916, 4,647,709, 4,925,994, and 5,210,343; and European Patent Application No. 126,669. Progress in the field of para halogenation of aromatic compounds notwithstanding, there remains a strong need to develop further improvements both in terms of product yield and selectivity.

BRIEF SUMMARY

The present invention provides methods and catalyst compositions for formation primarily of a para-chloroaromatic aromatic compound. The methods may be easily translated into a commercial operation.

In one embodiment of the present invention, method for ring-halogenating an aromatic compound comprises contacting the aromatic compound with chlorine or bromine in the presence of a catalyst composition, where the catalyst composition comprises: at least one salt comprising a metal selected from the group consisting of Group 13 metal; and a counterion derived from an acid having a pKa relative to water of 0 or greater; and at least one organic sulfur compound.

In a second embodiment of the present invention, a method for ring-chlorinating toluene or ortho-xylene comprises contacting toluene or o-xylene with chlorine in the presence of a catalyst composition, where the catalyst composition comprises: at least one salt comprising a metal selected from the group consisting of indium and thallium; and a counterion derived from an acid, said acid having a pKa relative to water of 0 or greater; and at least one organic sulfur compound selected from the group consisting of phenothiazine-N-carbonyl chloride, N-trifluoroacetylphenothiazine, 3-chloro-N-trifluoroacetylphenothiazine, and 3-trifluoromethyl-N-trifluoroacetylphenothiazine.

In a third embodiment of the present invention, a method for chlorinating toluene or o-xylene comprises contacting toluene or ortho-xylene with chlorine in the presence of a catalyst composition prepared by combining at least one metal salt selected from the group consisting of indium sulfide, indium telluride, thallium sulfide, and thallium oxalate; at least one organic sulfur compound; and a chlorine atom source.

A fourth embodiment of the invention is a catalyst composition prepared by combining (A) at least one salt comprising a metal selected from the group consisting of a Group 13 metal; and a counterion derived from at least one acid selected from the group consisting of those with an approximate pKa value relative to water of 0 or greater; (B) at least one organic sulfur compound and (C) a halogen atom source.

A fifth embodiment of the invention is a catalyst composition for chlorinating toluene or o-xylene, comprising at least one salt comprising a metal selected from the group consisting of thallium, indium, and gallium; and a counterion derived from a monocarboxylic acid, a dicarboxylic acid, hydrogen sulfide, hydrogen selenide, hydrogen telluride, and derivatives thereof; and at least one organic sulfur compound selected from the group consisting of phenothiazine-N-carbonyl chloride, N-trifluoroacetylphenothiazine, 3-chloro-N-trifluoroacetylphenothiazine or 3-trifluoromethyl-N-trifluoroacetylphenothiazine.

DETAILED DESCRIPTION

The embodiments described above have many advantages, such as providing catalyst compositions, and methods for using these catalyst compositions to promote efficient para-selective ring-halogenations of aromatic compounds, such as toluene and ortho-xylene.

Any aromatic compound may be chlorinated by the methods disclosed herein. Suitable aromatic compounds include monocyclic and polycyclic hydrocarbons, and substituted derivatives thereof. Non-limiting examples of monocyclic hydrocarbons include benzene, toluene, ortho-, meta-, and para-xylene; and 1,2,4,5-tetramethylbenzene. It is preferred that the aromatic hydrocarbon contains at least one $C_{1-4}$ alkyl substituent, preferably methyl, and that a para-position with respect to one of the alkyl groups be substituted with hydrogen. Most preferred are toluene and o-xylene.

In an embodiment of the invention, the aromatic compound is contacted with chlorine in the presence of a catalyst composition to effect reaction. For liquid aromatic compounds, chlorine gas is generally bubbled through the liquid reactant. A solvent may be used with liquid aromatic compounds, although solvent is ordinarily not necessary. For aromatic compounds that are solids at ambient temperatures, a solvent can be beneficially used. Typically, the reaction takes place preferably in the liquid phase rather than in the vapor phase.

For the sake of brevity, the constituents of the catalyst composition are defined as "components" irrespective of whether a reaction involving said constituents occurs before or during the chlorination reaction. Thus, the catalyst composition may include the reaction products derived from one or more of the components. Said reaction products may comprise chlorine, or hydrogen chloride, or chlorine and hydrogen chloride. Said reaction products may or may not be in admixture with one or more unreacted components remaining in the catalyst combination. Generally, the catalyst composition is obtained by combining components (A), (B), and (C). Component (A) of the catalyst composition is at least one compound, most often a salt, of a metal from Group 13 of the Periodic Table of Elements. Specific examples of the Group 13 metal include thallium, indium, and gallium. The salt may be of any acid—inorganic acid or organic acid, having a pKa relative to water of 0 or greater. Non-limiting examples of inorganic acid salts of Group 13 metals include but are not intended to be limited to the chalcogenide salts, such as indium sulfide, indium telluride, indium selenide, and thallium sulfide. Organic salts of the Group 13 metals are preferred since they are generally more soluble in the hydrophobic reaction medium present in ring-halogenation of aromatic compounds. Though it is not necessary for the metal salt to be soluble in the hydrophobic reaction medium, preferred salts include those that are at least partially soluble in the reaction medium. Included in this sub-category are salts where the anion (also hereinafter sometimes called the counterion) is derived from an acidic organic compound. Such salts have at least some solubility in a hydrophobic, organic solvent, such as for example, toluene and ortho-xylene. Illustrative examples of such acidic organic compounds include, but are not limited to, those with an approximate pKa value relative to water in a first embodiment of 0 or greater, in a second embodiment of 1 or greater, in a third embodiment of 2 or greater, in a fourth embodiment of 3 or greater in a fifth embodiment of 4 or greater, in a sixth embodiment of 5 or greater, in a seventh embodiment of 6 or greater, in an eighth embodiment of 7 or greater, in a ninth embodiment of 8 or greater, and in a tenth embodiment of 9 or greater. In some embodiments, the anion is derived from a carboxylic acid, such as for example, a monocarboxylic acid, or a dicarboxylic acid; a 2,4-dione, or a derivative thereof. By "2,4-dione" is meant a 1,3-dicarbonyl compound, including, but not limited to, a diketone or a beta-ketoester in which a carbon atom separates the two carbonyl groups, irrespective of the placement of said carbonyl groups in the molecule. Illustrative examples of derivatives of carboxylic acids include monocarboxylic acids, such as benzoic acid, acetic acid, trifluoroacetic acid, and the like; and illustrative examples of dicarboxylic acids include oxalic acid, malonic acid, and the like. Group 13 metal salts of the hydrogen chalcogenides, hydrogen sulfide, hydrogen selenide, and hydrogen telluride can also be used. Suitable non-limiting examples of 2,4-diones include halogenated derivatives, particularly the chlorinated or fluorinated derivatives. Other non-limiting examples of counterions derived from inorganic and organic acids include phosphate, phosphonate, alkoxide, phenoxide, and the like. Preferred examples of salts suitable as component (A) include, but are not limited to, indium sulfide, indium telluride, indium selenide, thallium sulfide, thallium oxalate, and indium oxalate.

Component (B) is at least one organic sulfur compound. Suitable compounds include dialkyl sulfide, a diaryl sulfide, a dialkyl disulfide, a diaryl disulfide, an alkyl mercaptan, an aryl mercaptan, a phenoxathiin, a thiophene dibenzothiophene, a thianthrene and a phenothiazine, including substituted derivatives thereof. Component B may also be a mixture of organic sulfur compounds.

A particularly preferred organic sulfur compound is phenothiazine-N-carbonyl chloride, having the formula

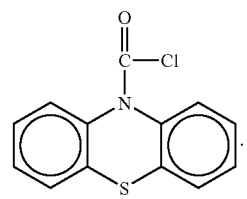

It may be synthesized by known methods such as the reaction of phenothiazine with phosgene. Also particularly effective is N-trifluoroacetylphenothiazine. Substituted analogs of N-trifluoroacetylphenothiazine, for example where the substituent is located on the aromatic ring, such as for example, 2-chloro-N-trifluoroacetylphenothiazine and 2-trifluoromethyl-N-trifluoroacetylphenothiazine are also effective.

Component (C) is a source of halide atoms such as dihalogen or hydrogen halide, such as hydrogen chloride. In an embodiment, the hydrogen halide can be a commercially available material, such as for example hydrogen chloride gas from a cylinder. In another embodiment, the hydrogen halide is generated in-situ from the electrophilic aromatic substitution reaction of an aromatic compound with a source of electrophilc halogen.

The method of the invention may be performed by contacting a mixture of the aromatic compound, component (A), and component (B) with chlorine, preferably in the liquid phase, most often at a temperature in the range of about 100° C., preferably about 5-50° C., and most preferably below 25° C. Preferably, the reaction mixture is protected from air and moisture by contact with an inert gas such as nitrogen or argon, and is shielded from exposure to ambient light to minimize chlorination of alkyl side chains on the aromatic compound. The term "light" in this context means radiation in the visible and ultraviolet regions of the spectrum. It is also important to shield the reaction mixture from moisture. The level of moisture in the aromatic compound to be halogenated should be preferably less than or equal to about 50 parts per million in one embodiment, more preferably less than or equal to about 25 parts per million in another embodiment.

On a preparative scale, contact is preferably accomplished by passing at least a portion, and more preferably substantially all of the chlorine through the reaction mixture. However, for screening purposes, it is often convenient to charge the chlorine to the head-space of the reaction system, and to remove by-product hydrogen chloride by applying a slight vacuum. The pressure at which the reaction is carried out may vary from sub-atmospheric to super-atmospheric, for example from about 0.5 up to about 10 atmospheres, although super-atmospheric pressure is generally not necessary. For screening purposes it has been found convenient to employ an excess of chlorine, typically up to about 50 mole %, and preferably about 10-30 mole % relative to the aromatic compound. It is also within the scope of the disclosure to generate chlorine in situ from a reagent such as thionyl chloride, sulfuryl chloride, phosgene, oxalyl chloride, and the like.

On a preparative scale, chlorine can simply be passed into the mixture with periodic sampling until the desired or maximum amount of the desired para-monochloroaromatic compound product has been produced, as determined by analytical methods known in the art; for example, gas chromatography. On a preparative scale, however, the use of excess chlorine is undesirable since it leads to over-chlorination. Typically, 25-100 mole %, preferably 50-90 mole % and most preferably 70-85 mole % of chlorine is employed, relative to the amount of aromatic compound being chlorinated. Under these conditions, the efficiency for use of the chlorine is nearly 100%, so excess chlorine inevitably generates over-chlorinated products.

The amount of component (A) is typically in a of range from about 0.005 to about 10.0%, and the amount of component (B) is in a range from about 0.005 to about 10.0% by weight based on the weight of the aromatic compound. Preferably, these ranges are respectively about 0.01-5.0% and about 0.01-0.1%, and most preferably 0.07-3.0% and about 0.05-0.1%. For the most part, the method of the present invention uses higher amounts of component (A) than that employed in traditional Lewis acid catalyzed chlorination reactions using a Lewis acid such as ferric chloride. By contrast, the amount of component (B) used according to the method of the present invention is generally lower relative to component (A) than when employed with art-recognized Lewis acid chlorination catalysts. The weight ratio of component (A) to component (B) is in various embodiments in a range of between about 2000:1 and 1:2000. The weight ratio of component (A) to component (B) is in some particular embodiments in a range of between about 2:1 and about 100:1; in other embodiments in a range of between about 3:1 and about 80:1; and in still other embodiments in a range of between about 3:1 and about 70:1.

In situations where conditions are optimized for production of the desired para-chloroaromatic compound, it may be possible to employ the chlorination product of the method of the invention directly for further purposes, for example as a chemical intermediate, without further purification. Further purification, if desired may be achieved by the use of one or more conventional purification techniques, including fractional distillation, fractional crystallization, and preparative-scale chromatographic methods. The halogenation methods described hereinabove can be carried out in a batch, a semi-batch, or continuous process.

The catalyst compositions taught herein may be employed for any reaction catalyzed by (1) the combination of (A) at least one salt comprising a metal selected from the group consisting of a Group 13 metal; and an organic counterion derived from at least one acidic compound selected from the group consisting of those with an approximate pKa value relative to water of at least about 0; and (B) at least one organic sulfur compound, or (2) a reaction product comprising (A) and (B), (3) the components (A), (B), and a reaction product comprising at least one of (A) or (B), or (4) (A), (B), and component (C). Illustrative applications of the catalyst compositions include, but are not limited to, halogenation reactions (e.g. chlorination, bromination, iodination) and Friedel-Crafts reactions.

The catalyst compositions and methods disclosed herein are especially useful for producing 4-chloro-ortho-xylene by the chlorination of ortho-xylene, and allow high ortho-xylene conversion while keeping the selectivity for mono-chloro-ortho-xylene at relatively high levels, and formation of over-chlorinated products at relatively lower levels. This increases the efficiency of recovery of purified 4-chloro-ortho-xylene by downstream operations, such as purification steps; and also decreases the cost of recovery and recycle of unreacted ortho-xylene by distillation.

EXAMPLES

The invention is illustrated by the following examples. All percentages are by weight. Example numbers with an asterisk ("*") or double asterisk ("**") after the number indicate control or comparative examples. The abbreviations "PNCC" and "DBT" stand for N-chlorocarbonyl phenothiazine and dibenzothiophene, respectively. "Conversion" is the percentage of ortho-xylene converted to chlorinated products. The abbreviation "mono-Cl" designates the amount of aromatically monochlorinated products (i.e., products in which the aromatic ring is monochlorinated as opposed to those in which the side chain is chlorinated) as a percentage of total chlorinated products, and "4-Cl" designates the amount of the 4-monochloro (p-chloro) isomer as a perce products.

EXAMPLES 1-7 AND CONTROL EXAMPLES 1-9

High throughput catalyst screening runs using PNCC as component (B). Chlorination runs were carried out with ortho-xylene or toluene as the aromatic compound.

Screening runs were performed at 10° C. and atmospheric pressure in a 48-well aluminum block reactor enclosed in an opaque a box for protection against ambient radiation. Argon-purged glass vials containing 352 mg (3.3 mmol) of ortho-xylene, various proportions of Group 13 metal salts (expressed in the Tables in weight percent (wt. %) salt based on ortho-xylene) and 0.02 wt. % (based on ortho-xylene) of PNCC were placed in the reactor wells. Vials were individually stirred. Chlorine (120 mole percent based on ortho-xylene) was added to the head space of each vial over a 20 minute period via a polytetrafluoroethylene gas manifold, and MONEL tubes having a 1.59 mm outer diameter (OD). A slight vacuum was applied to each reactor vial to remove excess chlorine as well as HCl formed in the reaction. Additionally, at the end of the reaction time, residual chlorine in the vials was eliminated by purging the vials with argon for 30 minutes. The composition of the reaction mixture in each vial was determined by gas chromatography. The results are given in Table I. In the Table, "A" stands for ortho-xylene, and "B" stands for toluene.

TABLE 1

| | | Metal salt | | Organic sulfur compound | | | | | | |
|---|---|---|---|---|---|---|---|---|---|---|
| Example | Ar-H | Identity | wt % | (1) | wt % (1) | (2) | wt % (2) | Conversion (%) | Mono-Cl (%) | 4-Cl (%) |
| 1 | A | $In_2S_3$ | 0.01 | PNCC | 0.1 | NA | NA | 93 | 95 | 75 |
| 1* | A | $In_2S_3$ | 0.01 | NA | NA | NA | NA | 35 | 91 | 58 |
| 2 | A | $In_2Te_3$ | 0.01 | PNCC | 0.1 | NA | NA | 96 | 94 | 75 |
| 2* | A | $In_2Te_3$ | 0.01 | NA | NA | NA | NA | 88 | 93 | 54 |

TABLE 1-continued

| Example | Ar-H | Metal salt Identity | wt % | Organic sulfur compound (1) | wt % (1) | (2) | wt % (2) | Conversion (%) | Mono-Cl (%) | 4-Cl (%) |
|---|---|---|---|---|---|---|---|---|---|---|
| 3 | A | Tl$_2$S | 0.01 | PNCC | 0.1 | NA | NA | 91 | 96 | 75 |
| 3* | A | Tl$_2$S | 0.01 | NA | NA | DBT | 0.1 | 90 | 97 | 69 |
| 4* | A | Tl$_2$S | 0.01 | NA | NA | NA | NA | 74 | 95 | 57 |
| 4 | A | Tl$_2$C$_2$O$_4$ | 0.01 | PNCC | 0.1 | NA | NA | 97 | 94 | 77 |
| 5* | A | Tl$_2$C$_2$O$_4$ | 0.01 | NA | NA | NA | NA | 83 | 96 | 54 |
| 6* | A | FeCl$_3$ | 0.01 | PNCC | 0.1 | NA | NA | 91 | 92.7 | 74.5 |
| 5 | B | In(TFA)$_3$ | 0.25 | PNCC | 0.1 | NA | NA | 76 | 99 | 54 |
| 7* | B | In(TFA)$_3$ | 0.25 | NA | NA | NA | NA | 80 | 99 | 45 |
| 6 | B | In$_2$S$_3$ | 0.25 | PNCC | 0.1 | NA | NA | 64 | 99 | 56 |
| 8* | B | In$_2$S$_3$ | 0.25 | NA | 0 | NA | NA | 6 | 94 | 35 |
| 7 | B | Tl$_2$S | 0.25 | PNCC | 0.1 | NA | NA | 76 | 99 | 56 |
| 9* | B | Tl$_2$S | 0.25 | NA | NA | NA | NA | 20 | 97 | 34 |
| 10* | B | FeCl$_3$ | 0.024 | PNCC | 0.02 | NA | NA | 85 | 95 | 56 |

It is evident from the results in Table I that satisfactory conversions and advantageous product distributions are obtained by the present invention. The results also show that the combination of the Group 13 metal salt of an acid having a pKa relative to water of 0 or greater, and PNCC gives higher ortho-xylene conversion, higher 4-chloro-ortho-xylene selectivity, and higher selectivity for monochlorinated ortho-xylene; as compared to when the metal salt alone is used.

EXAMPLE 8 and COMPARATIVE EXAMPLE 11

These Examples were carried out on a preparative scale using ortho-xylene (7 grams), In(acac)$_3$ (1.35 milligrams) and PNCC (10 mol equivalents relative to amount of In (acac)$_3$) for Example 8; and ortho-xylene (7 grams), FeCl$_3$ (0.89 milligrams), and PNCC (10 mol equivalents relative to amount of FeCl$_3$), for Comparative Example 11. The results are shown in Table 2. Aliquots of the reaction mixture were taken and analyzed after the indicated times shown in Table 2.

TABLE 2

| Example | Metal salt | Time (minutes) | Conversion (%) | 4-Cl (%) | Mono-Cl (%) |
|---|---|---|---|---|---|
| 8 | In(acac)$_3$ | 10 | 15 | 71 | 100 |
|   |   | 30 | 89 | 75 | 96 |
|   |   | 35 | 99 | 77 | 91 |
|   |   | 40 | 100 | 80 | 80 |
|   |   | 50 | 100 | 83 | 74 |
| 11* | FeCl$_3$ | 10 | 21 | 72 | 100 |
|   |   | 30 | 83 | 73 | 96 |
|   |   | 35 | 90 | 74 | 94 |
|   |   | 40 | 94 | 74 | 90 |
|   |   | 50 | 97 | 75 | 89 |

The results shown in Table 2 illustrate that with indium (acac)$_3$ metal salt, there is a significantly lower level of over-chlorinated products, as compared with the case when FeCl$_3$ is used as the metal salt.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:

1. A method for ring-chlorinating toluene or o-xylene, which comprises contacting toluene or ortho-xylene with chlorine in the presence of a catalyst composition, wherein said catalyst composition comprises:

at least one salt comprising a metal selected from the group consisting of indium and thallium; and a counterion derived from an acid, said acid having a pKa relative to water of 0 or greater; and at least one organic sulfur compound selected from the group consisting of phenothiazine-N-carbonyl chloride, N-trifluoroacetylphenothiazine, 3-chloro-N-trifluoroacetylphenothiazine, and 3-trifluoromethyl-N-trifluoroacetylphenothiazine.

2. The method of claim 1, wherein said at least one salt is selected from the group consisting of indium telluride, thallium sulfide, indium sulfide, thallium oxalate, and indium oxalate.

3. The method of claim 1, wherein the catalyst composition comprises at least one reaction product of said at least one salt, and said at least one organic sulfur compound.

4. The method of claim 1, wherein said contacting takes place in the liquid phase.

5. A method for chlorinating toluene or ortho-xylene which comprises contacting toluene or ortho-xylene with chlorine in the presence of a catalyst composition prepared by combining at least one metal salt selected from the group consisting of indium sulfide, indium telluride, thallium sulfide, and thallium oxalate; at least one organic sulfur compound; and a chlorine atom source.

6. The method of claim 5, wherein said organic sulfur compound is selected from the group consisting of phenothiazine-N-carbonyl chloride, N-trifluoroacetylphenothiazine, 3-chloro-N-trifluoroacetylphenothiazine, and 3-trifluoromethyl-N-trifluoroacetylphenothiazine.

7. The method of claim 5, wherein said catalyst composition comprises at least one reaction product of said at least one metal salt, and said at least one organic sulfur compound.

8. The method of claim 5, wherein said contacting takes place in the liquid phase.

9. The method of claim 5, wherein said chlorine atom source comprises molecular chlorine or hydrogen chloride.

* * * * *